United States Patent [19]

Gentelia et al.

[11] Patent Number: 5,824,002
[45] Date of Patent: Oct. 20, 1998

[54] TROCAR-CANNULA DEVICE

[75] Inventors: John S. Gentelia, Madison; Sharyn E. Longo, Frankfort; Thomas F. Bowers, Rome, all of N.Y.

[73] Assignee: Conmed Corporation, Utica, N.Y.

[21] Appl. No.: 752,387

[22] Filed: Nov. 20, 1996

Related U.S. Application Data

[63] Continuation of Ser. No. 532,053, Sep. 22, 1995, abandoned.

[51] Int. Cl.⁶ .................................................. A61M 5/178
[52] U.S. Cl. .......................... 604/164; 604/170; 604/264; 606/185
[58] Field of Search .................. 604/93, 104, 106–7, 604/164, 166, 263–4, 272, 170; 606/167, 185

[56] References Cited

U.S. PATENT DOCUMENTS

| | | | |
|---|---|---|---|
| 5,263,937 | 11/1993 | Shipp | 604/164 |
| 5,279,575 | 1/1994 | Sugarbaker . | |
| 5,300,070 | 4/1994 | Gentelia et al. . | |
| 5,350,393 | 9/1994 | Yoon | 606/185 |
| 5,372,588 | 12/1994 | Farley et al. | 606/185 |
| 5,575,804 | 11/1996 | Yoon | 606/185 |
| 5,580,344 | 12/1996 | Hasson | 604/104 |

FOREIGN PATENT DOCUMENTS

| | | | |
|---|---|---|---|
| 3814618 | 2/1989 | Germany | 604/164 |
| 843 744 | of 0000 | United Kingdom . | |
| 94 17845 | of 0000 | WIPO . | |

Primary Examiner—Michael Powell Buiz
Assistant Examiner—Ellen S. Tao
Attorney, Agent, or Firm—Larson & Taylor

[57] ABSTRACT

A trocar device, comprising a trocar cutting element, a surrounding insulating sheath, and a cannula surrounding the sheath, also includes an arrangement providing a substantially smooth transition between the sheath and cannula at the distal end of the cannula during the insertion of the trocar device into a patient so as to reduce drag on the device at the transition. In one embodiment, the sheath includes a shaped portion of enlarged diameter, and the cannula includes, at the distal end thereof, inwardly directed slits forming corresponding resilient leaf members which engage the shaped portion to provide the smooth transition. The shaped portion includes oppositely tapered surfaces meeting at a common apex. In another embodiment, an expandable section, when expanded, provides the smooth transition.

7 Claims, 5 Drawing Sheets

TROCAR-CANNULA DEVICE

This application is a continuation of application Ser. No. 08/532,053 filed Sep. 22, 1995 now abandoned.

FIELD OF THE INVENTION

The present invention relates to trocar-cannula device wherein a trocar inserted within the bore of the cannula is used to create an opening in the tissue of a patient in which the cannula is disposed and secured.

BACKGROUND OF THE INVENTION

Mechanical trocar assemblies used in laparoscopic surgery and like procedures include a trocar element or obturator which is used to puncture the abdominal wall and an outer sheath or cannula which surrounds the trocar element and which is disposed in place in the opening created by the trocar element. Once the cannula is in place, and with the trocar removed, narrow diameter medical elements can be inserted through the cannula to perform various medical procedures.

Referring to FIG. 1, a typical mechanical trocar assembly is shown which is generally denoted 10 and which includes a trocar element or obturator 12 and an outer cannula 14. The trocar element 12 includes a pointed, sharpened distal end 16 which, in a common commercial form illustrated in FIGS. 2 and 3, includes the sector shaped cutting faces 16a, 16b and 16c terminating in a point, as shown. The relatively long sharpened cutting edges formed at the intersections of the faces 16a, 16b and 16c are necessary to ensure penetration through the abdominal wall, and because this wall includes muscle, very substantial forces (as great as 50 to 20 pounds) can be required to effect penetration through the wall. This creates problems of safety since organs within the abdominal cavity can be punctured or otherwise damaged.

The latter problem and solutions thereto are discussed in somewhat more detail in commonly assigned copending U.S. patent application Ser. No. 08/187,127 (based on an application filed on Mar. 17, 1992) now U.S. Pat. No. 5,599,348, and commonly assigned U.S. Pat. No. 5,300,070 (Gentelia et al) both of which disclose electrosurgical trocars and trocar systems. The electrosurgical trocars disclosed in this application and patent include an electrosurgical cutting element and a surrounding cannula, and, as is discussed in the application and patent, these electrosurgical trocars provide important advantages over conventional mechanical trocars.

A problem common to both mechanical and electrosurgical trocars concerns the effect of the transition between the trocar element and the cannula. Referring to FIG. 1 and FIG. 4, it will be appreciated that although the amount shown is exaggerated in the drawings, some clearance must be provided between the outer diameter of the trocar 12 and the inner diameter of the cannula 14, and that, as shown in FIG. 4, an increased gap or spacing, indicated at S, will occur when the trocar element 12 is inserted off axis so as to engage against one wall of the cannula 14. Because of the sharpened intersecting edges, a mechanical trocar such as illustrated in FIGS. 1 to 4 will create three slits and three corresponding "flaps" in the area at which the trocar point enters. While this has disadvantages as compared with an electrosurgical trocar, such as increased bleeding at the entry site, entry of the cannula may be somewhat easier because of these slits and resulting flaps.

With an electrosurgical trocar the basic procedure is to bore a very small hole with the electrosurgical cutting element of the trocar and then dilate the opening using the tapered slanted sides of the cutting element and associated sheath. Because of the relatively large transition at the cannula (which can be exacerbated where the trocar is offset as discussed above in connection with FIG. 4), the device can "hang up" on the tissue at this transition, i.e., the device can be impeded at the epidermis and can shave tissue going in. Although the problem has been discussed relative to the transition at the cannula, which is the transition between the sheath and cannula with an electrosurgical trocar, a similar problem can occur at the transition between the sheath and the trocar cutting element. This impeding effect at these transitions creates an inconsistency in the pressure required to insert the device, i.e., in the downward force necessary to penetrate the abdominal wall that is experienced by the surgeon. It is noted that with the electrosurgical trocar described above, once the cutting element of the trocar penetrates the peritoneum, the electrosurgical generator is cut off but mechanical dilation continues. Because of the danger to the internal organs discussed above, the surgeon is reluctant to exert too much force and this situation can cause apprehension on the part of a surgeon regarding use of an electrosurgical trocar.

SUMMARY OF THE INVENTION

In accordance with the invention, a trocar device is provided which comprises a trocar cutting element such as an electrosurgical cutting element, an insulating sheath surrounding the cutting element, a cannula surrounding the sheath and having an inner diameter greater than the outer diameter of the sheath, and transition means for providing a substantially smooth transition between the sheath and cannula at the distal end of the cannula during the insertion of the trocar device into a patient so as to reduce drag on the device at the transition.

According to one preferred embodiment, the sheath includes a shaped portion of enlarged diameter, and the cannula includes, at the distal end thereof, a plurality of inwardly directed slits forming a plurality of resilient leaf members which engage the shaped portion to provide said smooth transition and which, in cooperation with the shaped portion, enable withdrawal of the sheath. Preferably, the shaped portion includes first and second oppositely tapered surfaces meeting at a common apex of said enlarged diameter.

In a further advantageous implementation, the sheath device further comprises means for providing a further smooth transition between the cutting element and the sheath at the distal end of the sheath. In this implementation, the trocar element also includes a shaped portion of enlarged diameter, and the sheath includes, at the distal end thereof, a plurality of inwardly directed slits forming a plurality of resilient leaf members which engage the shaped portion of the trocar element to provide said further smooth transition. Preferably, the shaped portion of the trocar element also includes first and second oppositely tapered surfaces meeting at a common apex of enlarged diameter.

In a further preferred embodiment, the transition means includes expandable means for, when expanded, providing said smooth transition. Advantageously, the expandable means includes a resilient annular element of a low durometer material, preferably a rubber grommet. In this embodiment, the sheath preferably comprises a body member and a separate tip member movable with respect to the body member, the tip member including a shoulder against which one end of the annular element bears, and the body member including a distal end against which the other end of the annular element bears. The body member advantageously includes means defining at least one aperture in the sidewall thereof, and the tip member includes at least one leaf or spring member including a projection for engaging the aperture defining means in a rest condition of the device, the at least one projection being disengaged from the aperture defining means in response to pressure exerted on the sheath during insertion of the device into a patient.

In an advantageous implementation of this embodiment, the device comprises remotely operable means for controlling expansion of the expandable means. In one preferred implementation, the remotely operable means includes actuation means for producing axial compression of the resilient annular element to effect outward expansion thereof. In a further preferred implementation, the annular element includes a fluid chamber and the remotely operable means includes a controllable fluid pressure source for varying the fluid pressure in the chamber to effect such expansion of the annular element.

In a further advantageous implementation of this embodiment, the expandable means comprises a plurality of pivoted leaf members. Preferably, the device further comprises remotely operable means for producing pivoting of said pivoted leaf members. In one implementation, the remotely operable means comprises means for exerting a pushing force on said leaf members to cause pivoting thereof and in another implementation, the remotely operable means comprises means for exerting a pulling force on the leaf members to cause pivoting thereof.

Other features and advantages of the invention will be set forth in, or apparent from, the following detailed description of preferred embodiments of the invention.

BRIEF DESCRIPTION OF THE DRAWINGS

As described above.

DESCRIPTION OF THE PREFERRED EMBODIMENTS

Figure 1:
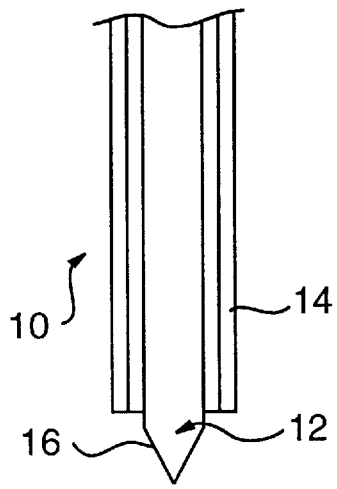
FIG. 1 is a cross sectional view of a portion of a mechanical trocar-cannula device.
Figure 2:
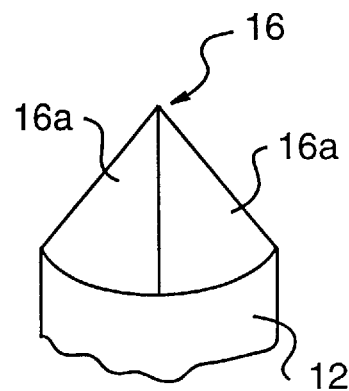
FIGS. 2 and 3 are a perspective view and a top plan view, respectively, of the trocar of FIG. 1.
Figure 3:
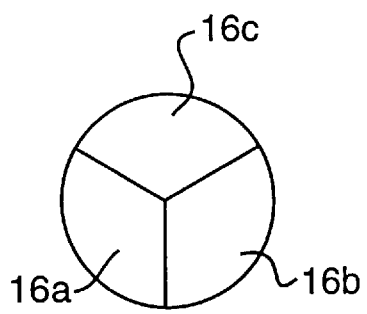
Figure 4:
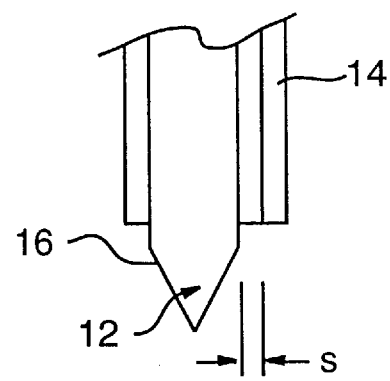
FIG. 4 is a detail of a portion of FIG. 1, showing the trocar cutting element in a different position.
Figure 5:
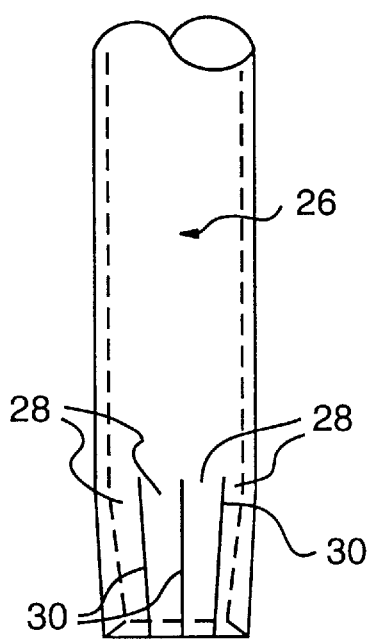
FIG. 5 is a side elevational view of a cannula constructed in accordance with a first preferred embodiment of the invention.
Figure 6:
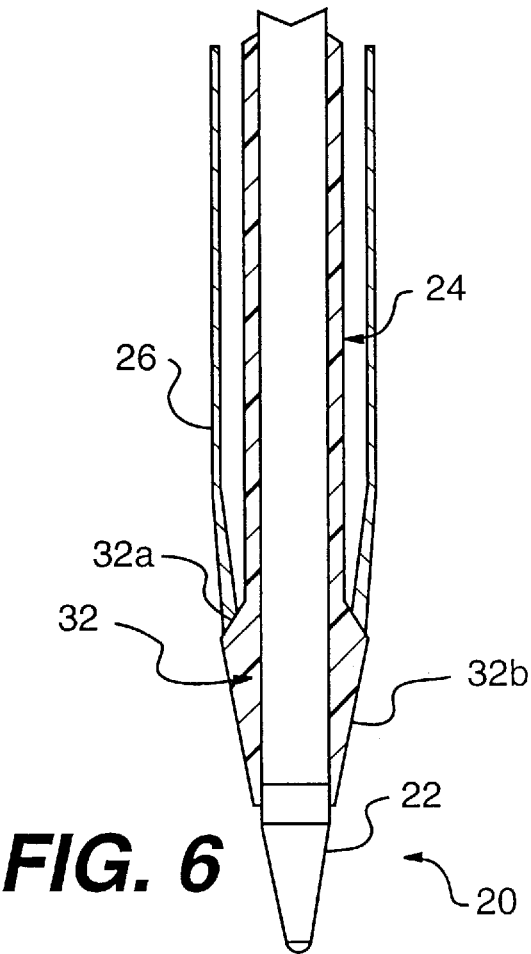
FIG. 6 is a side elevational view, partially in cross section, of a trocar-cannula device constructed in accordance with the embodiment of FIG. 5.

Referring to FIGS. 5 and 6, a first embodiment trocar-cannula device of the invention is shown. The overall device is shown in FIG. 6 and is generally denoted 20. Device 20 includes a central electrosurgical trocar cutting element 22 surrounded by an insulating trocar sheath 24. Trocar element 22 comprises a metal rod of a now conventional construction disclosed, for example, in commonly assigned U.S. Pat. No. 5,300,070 (Gentelia et al.) mentioned above. A cannula 26 surrounds sheath 24.

As perhaps can be best seen in FIG. 5, cannula 26 includes inwardly inclined leaves or fingers 28 separated from each other by slots or slits 30 provided in the distal terminal edge of cannula 26 and extending longitudinally inwardly therefrom. Sheath 24 includes an enlarged portion 32 near the distal end formed by intersecting inclined or sloping surfaces 32a and 32b. The diameter of the terminal portion of the cannula 26 is smaller than the largest diameter of the sheath 24 which is the diameter at the apex formed at intersection of surfaces 32a and 32b. When the combination of sheath 24 and trocar element 22 is inserted into the cannula 26, the distal end of cannula 26 will expand until the highest point, i.e., greatest diameter, of sheath 24 clears the cannula. Thus, there will be a smooth transition provided at the junction between the sheath 24 and cannula 26, and the expansion action at the distal end of cannula 26 will eliminate any drag or interference caused by the transition at that point.

The angle of slope or inclination of surface 32a, and the flexibility of the fingers 28 are chosen such that the combination of sheath 24 and trocar element 22 can be withdrawn out through cannula 26 against the inwardly directed biassing force of leaf members or fingers 28.

Figure 7:
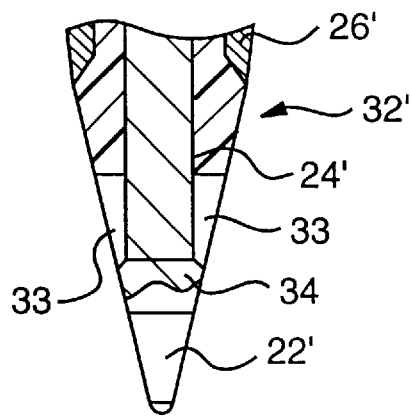
FIG. 7 is a view, similar to that of FIG. 6, of a portion of a trocar-cannula device, illustrating a variation on the embodiment of FIGS. 5 and 6.

Referring to FIG. 7, wherein elements corresponding to those of FIGS. 5 and 6 have been given the same reference numerals with a prime attached, a variation on the embodiment of FIGS. 5 and 6 is shown in which sheath 24' is slotted in a similar way to cannula 26 of FIGS. 5 and 6, as indicated by slots 33, and trocar element 22' has been provided with an enlarged portion 34 similar to sheath 24 of FIG. 5 and 6. In other words, in the embodiment of FIG. 7 the sheath-trocar element transition has been modified in the same way as the cannula-sheath transistor in FIGS. 5 and 6.

Figure 8:
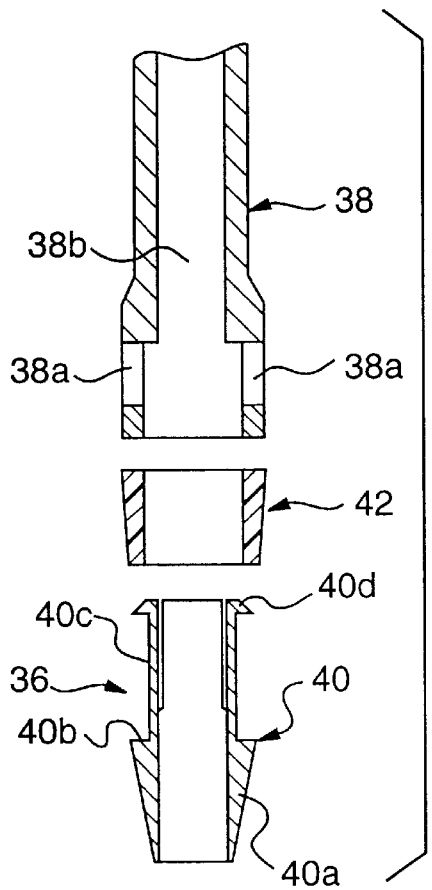
FIG. 8 is an exploded cross sectional view of a trocar sheath constructed in accordance with a further preferred embodiment of the invention.
Figure 9:
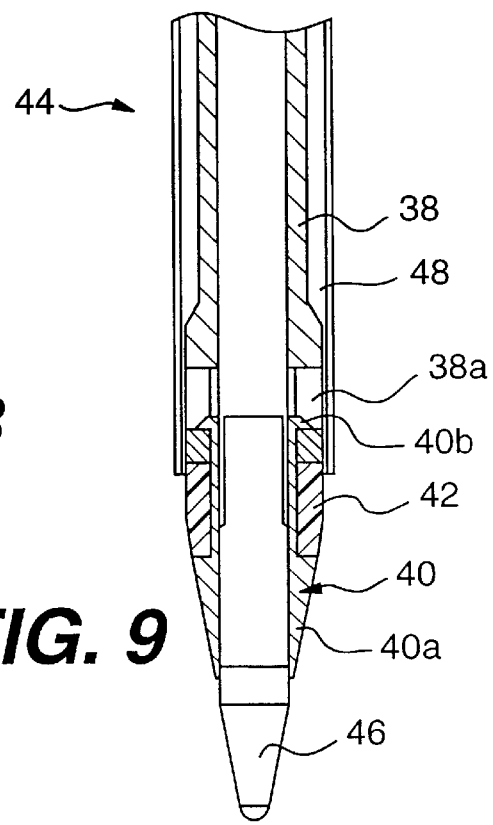
FIGS. 9 and 10 are side elevational views of the overall trocar-cannula device of the embodiment of FIG. 8, showing two different stages in the operation of the device.
Figure 10:
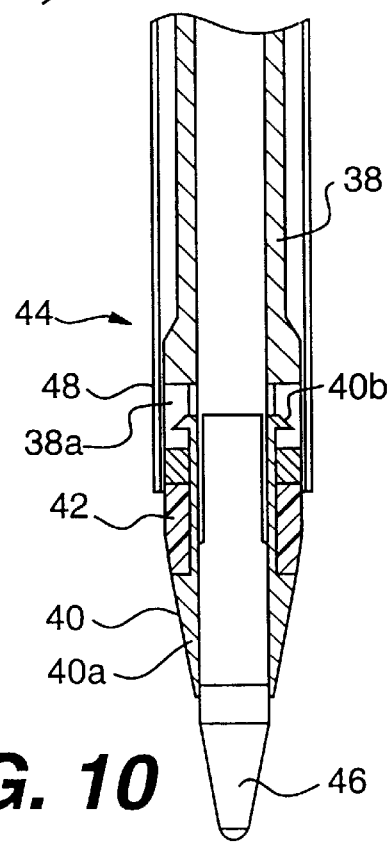

Referring to FIGS. 8 to 10, a further embodiment of the invention is shown. In this embodiment, as shown in FIG. 8, a three part sheath 36 is use which includes a body or proximal sheath member 38, a tip or distal sheath member 40, and a resilient annular grommet or ring 42. The latter is made of rubber or the like, preferably of a low durometer number, and interconnects members 38 and 40. Tip member 40 includes a tapered end portion 40a including an inwardly disposed shoulder 40b and a plurality of spring fingers 40c terminating in outwardly directed projections 40d. Body member 38 includes a plurality of slots or apertures 38a in the sidewall thereof near the distal end. As shown in FIG. 9, when sheath 36 is assembled, fingers 40c enter into the bore 38b in member 38, with projections 40d engaging in apertures 38a, and the low durometer rubber grommet 42 is captured between the distal end of body member 38 and the shoulder 40b of tip member 40.

FIG. 9 also shows the overall trocar device, which is generally denoted 44, including an inner trocar element 46 and an outer cannula 48 surrounding sheath 36.

In operation, when the trocar device is inserted into the abdominal wall of a patient, the normal entry force exerted against the sheath tip member 40 causes the rubber grommet 42 to expand beyond the cannula transition, thereby providing a smooth surface at that transition as shown in FIG. 10. In this embodiment, because of the expanding diameter of grommet 42, the dilated hole produced by device 44 will be made larger, thereby permitting a substantially smoother insertion.

It will be appreciated by those skilled in the mechanical arts that although a rubber grommet has been employed in the illustrated embodiment, other mechanisms including, e.g., mechanically actuated leaf members, can be used for this purpose. Further, a second grommet or ring arrangement can also be provided at the transition between sheath 38 and trocar element 46.

Figure 11:
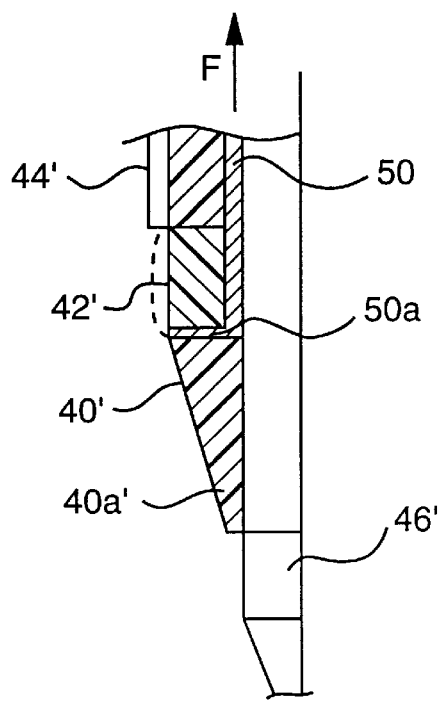
FIG. 11 is a one-half cross section of a first alternative implementation of the embodiment of FIGS. 8 to 10.

A further alternative embodiment to that illustrated in FIGS. 8 to 10 is shown in FIG. 11 wherein like elements are given the same reference numerals with primes attached. In this embodiment, a mechanical actuator member 50 is used to exert an upward force, denoted F, which acts on grommet 42' to cause outward or lateral expansion thereof, as indicated in dashed lines. In the illustrated embodiment actuator member includes a lateral extension 50a that acts against the bottom of grommet 42' but it will be appreciated that other mechanisms can also be used. A "squeeze handle" or other operating mechanism (not shown) can be used to provide the upward force that produces the required squeezing or compression of grommet 42' to cause lateral expansion thereof. With this approach, outward or lateral expansion of the grommet 40' can be remotely controlled by the operator, and this permits the operator to "nibble" the device 44' into place using very little downward pressure.

Figure 12:
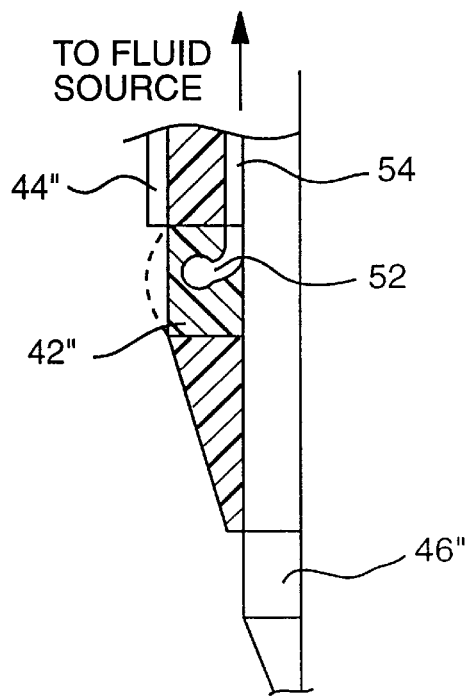
FIG. 12 is a one-half cross section of a second alternative implementation of the embodiment of FIGS. 8 to 10.

A further alternative embodiment is shown in FIG. 12 which is similar to that of FIG. 11 and in which like elements have been given the same reference numerals with double primes attached. In this embodiment, a fluid chamber or reservoir 52 is provided in grommet 42" and is connected by tubing 54 to a control or fluid pressure source (not shown). By increasing the pressure within chamber 52 grommet 42" can be caused to laterally expand in a manner similar to the embodiments discussed above.

Figure 13:
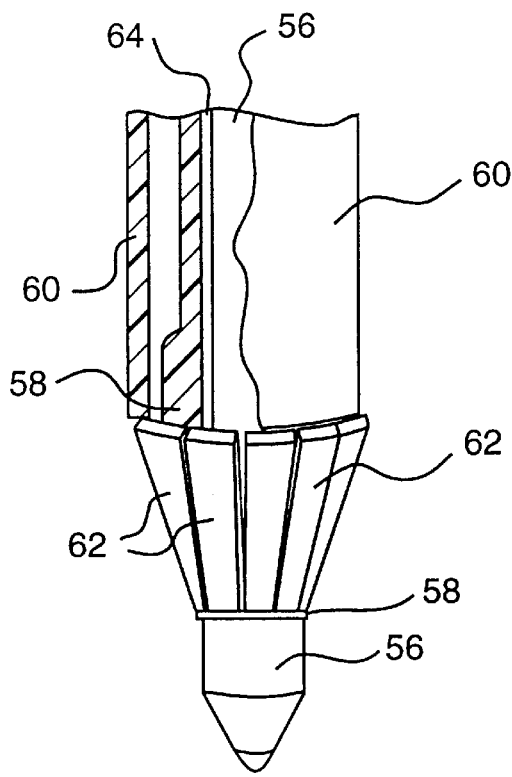
FIG. 13 is a side elevational view, partially in cross section and partially broken away, of a further embodiment of the invention.
Figure 14:
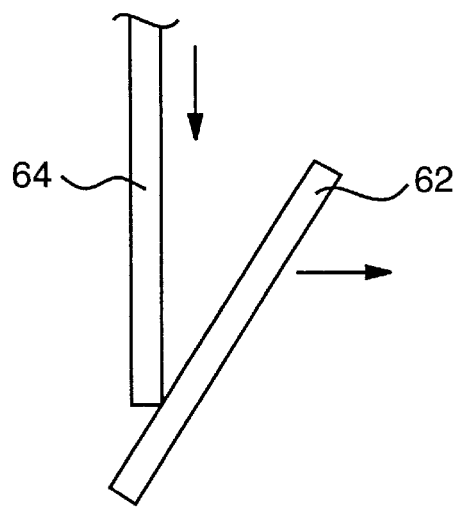
FIG. 14 is a diagram illustrating the operation of the embodiment of FIG. 13.

Referring to FIG. 13, a further alternative embodiment of the invention is shown. In this embodiment, the trocar element is denoted 56, the sheath 58 and the cannula 60. A plurality of hinged leaf members 62 are mounted at the distal end of sheath 58 and hinged at that end so that the other ends of leaf members 62 are free to move. A cylindrical actuator sleeve 64 is positioned within sheath 58 so as to exert a downward force on leaf members 62 and to thus cause the upper ends thereof to pivot outwardly. This is illustrated in the schematic representation or diagram shown in FIG. 14 for one leaf member 62. With this arrangement, an effect similar to that of the embodiments of FIGS. 11 and 12 can be produced by an operator by exerting, or causing to be exerted, a downward force on sleeve 64.

Figure 15:
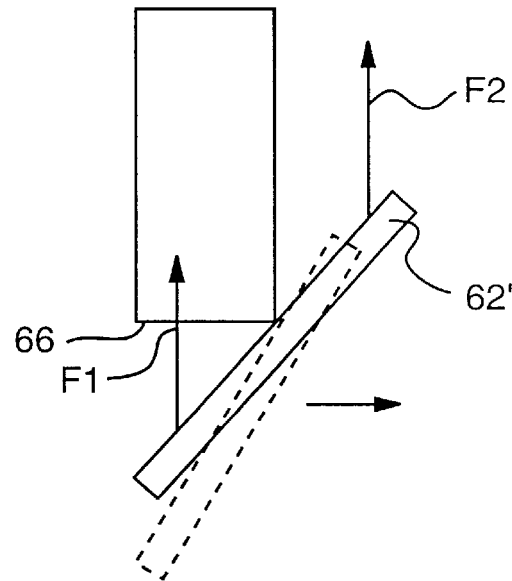
FIG. 15 is a diagram illustrating the operation of an alternative implementation of the embodiment of FIG. 13.

It will be appreciated that actuator arrangements other than a downwardly acting sleeve corresponding to sleeve 64 can be employed and, referring to FIG. 15, an arrangement is shown schematically wherein an upward force, such as that indicated at F1 or at F2, is exerted to pull leaf member 62' up against an abutment surface 66 to cause pivoting or splaying out of leaf member 62'.

Figure 16:
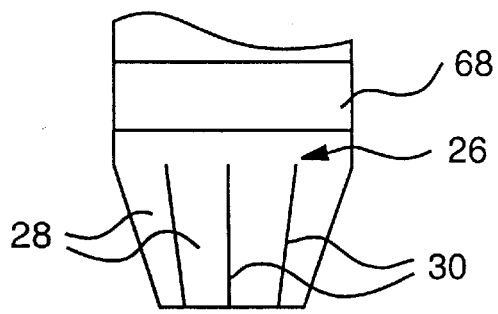
FIG. 16 is a detail of an alternative embodiment of the cannula shown in FIG. 5.
Figure 17:
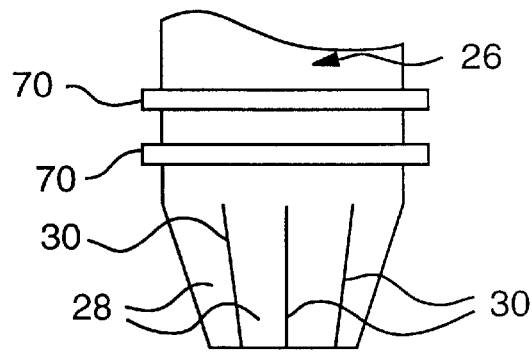
FIG. 17 is a detail of a further alternative embodiment of the cannula shown in FIG. 5.

Referring to FIGS. 16 and 17, there are shown alternative embodiments of cannula 26 illustrated in FIG. 5. In FIG. 16, a portion or region 68 of the surface of cannula 26 is textured or roughened, either during the molding process or afterwards, by bead blasting or the like. The surface portion 68 so created assists in retaining cannula in place after the trocar and sheath have been removed. In this regard, it has been found that while such a textured or roughened surface region 68 does not substantially hinder insertion of the cannula because of the provision of surface region 68, the cannula, once in place, wants to stay where it is, i.e., tends to be retained in place by the associated frictional forces generated at region 68. A similar retaining or holding effect is provided in FIG. 17 by a pair of rings 70. In a specific exemplary embodiment, roughened region 68 and rings 70 are provided about ¼ to ½ inch above leaves 28.

It will also be appreciated that while the present invention has been described relative to an electrosurgical trocar, i.e., one having an electrosurgical cutting element, it is also applicable to other trocars and trocar assemblies.

Although the present invention has been described relative to specific exemplary embodiments thereof, it will be understood by those skilled in the art that variations and modifications can be effected in these exemplary embodiments without departing from the scope and spirit of the invention.

What is claimed is:

1. A trocar device comprising a trocar element having a blunt tip, a sheath affixed to and surrounding the trocar element such that at least said blunt tip of said trocar element is exposed and so that said trocar element and said sheath are movable together as a unit, and a cannula surrounding the sheath and having a distal end, said sheath including expandable means, expandable laterally outwardly responsive to an external force being exerted thereon and collapsible when said force is removed, for providing, when expanded, a substantially smooth, at least substantially continuous transition between said sheath and said cannula at the distal end of said cannula during the insertion of said trocar device into a patient so as to reduce drag on the device at said transition and for enabling, when collapsed, removal of said sheath and trocar element through said cannula, said cannula having a longitudinal axis and leaf members each comprising substantially planar elements having lateral edges and said planar elements being disposed around said longitudinal axis in a substantially continuous annular configuration with the lateral edges thereof in side by side relation.

2. A device as claimed in claim 1 further comprises remotely operable means for controlling expansion of said expandable means.

3. A device as claimed in claim 1, wherein said leaf member are pivoted.

4. A device as claimed in claim 3, further comprising remotely operable means for producing pivoting of said pivoted leaf members.

5. A device as claimed in claim 4, wherein said remotely operable means comprises means for exerting a pushing force on said leaf members to cause pivoting thereof.

6. A device as claimed in claim 3 wherein said planar elements taper outwardly in a direction away from said blunt tip.

7. A trocar device comprising a trocar element having a blunt tip, a sheath affixed to and surrounding the trocar element such that at least said blunt tip of said trocar element is exposed and so that said trocar element and said sheath are movable together as a unit, and a cannula surrounding the sheath and having a distal end, said sheath including expandable means, expandable laterally outwardly responsive to an external force being exerted thereon and collapsible when said force is removed, for providing, when expanded, a substantially smooth transition between said sheath and said cannula at the distal end of said cannula during the insertion of said trocar device into a patient so as to reduce drag on the device at said transition and for enabling, when collapsed, removal of said sheath and trocar element through said cannula, said expandable means comprising a plurality of pivoted leaf members, and further comprising remotely operable means for producing pivoting of said pivoted leaf members, said remotely operable means comprising means for exerting a pulling force on said leaf members to cause pivoting thereof.

* * * * *